United States Patent
Chen et al.

(10) Patent No.: US 10,001,516 B2
(45) Date of Patent: Jun. 19, 2018

(54) REDUCING NOISE AND ENHANCING READOUT THROUGHPUT IN SENSOR ARRAY

(71) Applicant: International Business Machines Corporation, Armonk, NY (US)

(72) Inventors: Chia-Yu Chen, White Plains, NY (US); Shu-Jen Han, Cortlandt Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/014,350

(22) Filed: Feb. 3, 2016

(65) Prior Publication Data

US 2017/0219519 A1  Aug. 3, 2017

(51) Int. Cl.
| | |
|---|---|
| *G01R 27/08* | (2006.01) |
| *G01R 27/02* | (2006.01) |
| *G01N 27/414* | (2006.01) |
| *G01N 27/02* | (2006.01) |
| *G01N 33/00* | (2006.01) |

(52) U.S. Cl.
CPC .............. *G01R 27/02* (2013.01); *G01N 27/02* (2013.01); *G01N 27/4148* (2013.01); *G01N 33/0031* (2013.01)

(58) Field of Classification Search
CPC ..... G01N 27/02; G01N 27/4148; G01R 27/02
USPC .................................................. 324/691, 693
See application file for complete search history.

(56) References Cited

U.S. PATENT DOCUMENTS

| | | | |
|---|---|---|---|
| 3,575,557 A | 4/1971 | McCowen | |
| 4,800,885 A | 1/1989 | Johnson | |
| 7,939,338 B2 | 5/2011 | Wang et al. | |
| 8,053,244 B2 | 11/2011 | Ryan et al. | |
| 8,124,463 B2 | 2/2012 | Chen et al. | |
| 8,293,607 B2 | 10/2012 | Afzali-Ardakani et al. | |
| 8,405,385 B2 | 3/2013 | Hall et al. | |
| 9,091,648 B2 | 7/2015 | Afzali-Ardakani et al. | |
| 2005/0258821 A1* | 11/2005 | Wang ............... | B82Y 25/00 324/200 |
| 2011/0048508 A1 | 3/2011 | Afzali-Ardakani et al. | |

(Continued)

OTHER PUBLICATIONS

Balasubramanian et al., "Biosensors based on carbon nanotubes," Anl. Bioanal. Chem., 385: 452-468 (Mar. 2006).

(Continued)

*Primary Examiner* — Amy He
(74) *Attorney, Agent, or Firm* — Vazken Alexanian; Michael J. Chang, LLC (57) ABSTRACT

Frequency division multiplexing-based techniques for FET-based sensor arrays are provided. In one aspect, a sensor device includes: an array of FET-based sensors, wherein the sensors are grouped into multiple channels, and wherein each of the sensors includes an insulator on a substrate, a local gate embedded in the insulator, a channel material over the local embedded gate, and source and drain electrodes in contact with opposite ends of the channel material, and wherein a surface of the channel material is functionalized to react with at least one target molecule. The sensors in a given channel can be modulated (via the local gate) to enable the signal read out from the channel to be divided in the frequency domain based on the different frequencies used to modulate the sensors.

19 Claims, 4 Drawing Sheets

(56) References Cited

U.S. PATENT DOCUMENTS

2012/0031551 A1  2/2012  Hsu
2014/0363643 A1  12/2014  Afzali-Ardakani et al.

OTHER PUBLICATIONS

Balandin, "Low-frequency 1/f noise in graphene devices," Nature Nanotechnology 8, 549-555 (Aug. 2013).
Kichambare et al., "Biosensing using Carbon Nanotube Field-effect Transistors," Nanotechnologies for the Life Sciences, vol. 8, pp. 1-26 (Sep. 2007).
Han et al., "A high-density magnetoresistive biosensor array with drift-compensation mechanism," International Solid-State Circuits Conference, ISSCC, Feb. 2007, Paper 8.9 (3 pages).
D.A. Hall et al., "GMR biosensor arrays: A system perspective." Biosensors and Bioelectronics, vol. 25, No. 9, Feb. 2010, pp. 2051-2057.
Q. Cao et al., "Fringing-field dielectrophoretic assembly of ultra-high-density semiconducting nanotube arrays with a self-limited pitch," Nature Communications, vol. 5, No. 5071, Sep. 2014, 7 pages.
H. Park et al., "High-density integration of carbon nanotubes via chemical self-assembly," Nature Nanotechnology, vol. 7, No. 12, Oct. 2012, pp. 787-791.
Han et al., "Graphene radio frequency receiver integrated circuit," Nature Communications, vol. 5, No. 3086, Jan. 2014, 6 pages.
H. Wang et al., "Black phosphorus radio-frequency transistors," Nano Letters, vol. 14, No. 11, Oct. 2014, pp. 6424-6429.

\* cited by examiner

REDUCING NOISE AND ENHANCING READOUT THROUGHPUT IN SENSOR ARRAY

FIELD OF THE INVENTION

The present invention relates to sensor arrays, and more particularly, to field-effect transistor (FET)-based chemical and biosensor arrays with sensors having local embedded gates and frequency division multiplexing (FDM)-based techniques for operating the array.

BACKGROUND OF THE INVENTION

Materials such as carbon nanotubes and graphene are excellent materials for fast chemical sensing or bio-sensing due to their large surface-to-volume ratio and electronic sensitivity to surface molecules. See, for example, Balasubramanian et al., "Biosensors based on carbon nanotubes," Anl. Bioanal. Chem., 385: 452-468 (March 2006).

However, the sensitivity of conventional sensors is limited by low-frequency 1/f noise. See, for example, Balandin, "Low-frequency 1/f noise in graphene devices," Nature Nanotechnology 8, 549-555 (August 2013). Therefore, it would be desirable to be able to increase the signal-to-noise ratio to enhance detection sensitivity.

Further, in most applications data is collected from multiple sensors. The question then becomes how to extract data from the sensors in the most efficient manner. Techniques such as time-division multiplexing are often employed to reduce readout time. However, time-division multiplexing can only reduce readout to a certain limit. Therefore, it would be desirable to be able to speed up readout for high density sensor arrays.

SUMMARY OF THE INVENTION

The present invention provides frequency division multiplexing (FDM)-based techniques for field-effect transistor (FET)-based chemical and biosensor arrays having local embedded gates. In one aspect of the invention, a sensor device is provided. The sensor device includes: an array of FET-based sensors, wherein the sensors are grouped into multiple channels, and wherein each of the sensors includes an insulator on a substrate, a local gate embedded in the insulator, a channel material over the local embedded gate, and source and drain electrodes in contact with opposite ends of the channel material, and wherein a surface of the channel material is functionalized to react with at least one target molecule; transimpedance amplifiers connected to outputs of the channels; and a time division multiplexer connected to outputs of the transimpedance amplifiers, wherein the source electrodes of the sensors in a given one of the channels are interconnected, and wherein the drain electrodes of sensors in the given channel are interconnected to a given one of the transimpedance amplifiers.

In another aspect of the invention, a sensing method is provided which includes the steps of: forming a sensor device having: i) an array of FET-based sensors, wherein the sensors are grouped into multiple channels, and wherein each of the sensors includes an insulator on a substrate, a local gate embedded in the insulator, a channel material over the local embedded gate, and source and drain electrodes in contact with opposite ends of the channel material, and wherein a surface of the channel material is functionalized to react with at least one target molecule, ii) transimpedance amplifiers connected to outputs of the channels, and iii) a time division multiplexer connected to outputs of the transimpedance amplifiers; interconnecting the source electrodes of the sensors in a given one of the channels; interconnecting the drain electrodes of sensors in the given channel to a given one of the transimpedance amplifiers; modulating the sensors in the given channel to different frequencies; reading a signal from the given channel; and dividing the signal in the frequency domain based on the different frequencies used to modulate the sensors.

A more complete understanding of the present invention, as well as further features and advantages of the present invention, will be obtained by reference to the following detailed description and drawings.

DETAILED DESCRIPTION OF PREFERRED EMBODIMENTS

Provided herein are (graphene, carbon nanotubes, or other nanowire/nanosheet materials-based) sensor arrays and techniques for operation thereof which solve the above-described drawbacks associated with conventional practices. For instance, as will be described in detail below, the present sensors use separate (i.e., local) embedded gates for each sensor, which permits the modulation of each sensor separately at much higher frequencies to 1) reduce low-frequency 1/f noise, and 2) to institute what is referred to herein as "frequency division multiplexing" or FDM whereby the sensors in a group of sensors are (via the local embedded gates) individually modulated to a different frequency.

Figure 1:
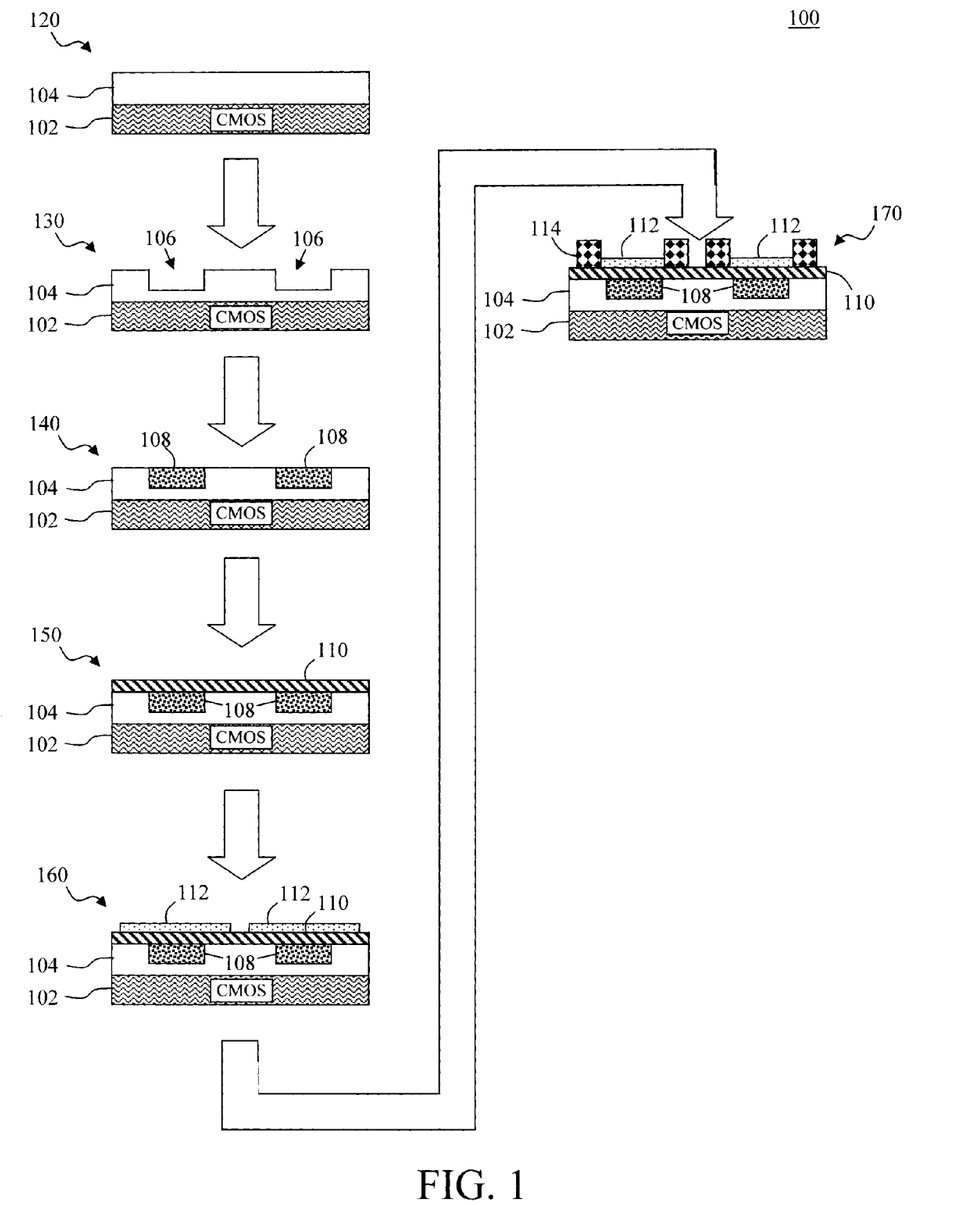
FIG. 1 is a cross-sectional diagram illustrating an exemplary methodology for forming a sensor array according to an embodiment of the present invention.

FIG. 1 is a diagram illustrating an exemplary methodology 100 for forming the present sensor arrays. It is notable that while FIG. 1 depicts the formation of two adjacent sensors, the same process applies to the fabrication of multiple rows/columns of sensors (see below).

As shown in step 120, the sensor can be constructed on any suitable substrate 102. For instance, the substrate 102 can be a semiconductor substrate such as a silicon (Si), strained Si, silicon carbide (SiC), germanium (Ge), silicon germanium (SiGe), silicon-germanium-carbon (SiGeC), Si alloys, Ge alloys, gallium arsenide (GaAs), indium arsenide (InAs), and/or indium phosphide (InP) substrate. The substrate 102 may be configured as a bulk wafer, or as a semiconductor-on-insulator or SOI wafer. As is known in the art, an SOI wafer includes an SOI layer separated from a handle substrate by a buried insulator. When the buried insulator is an oxide, the buried insulator may also be referred to as a buried oxide or BOX.

Further, as shown in FIG. 1, the substrate 102 may optionally include pre-fabricated complementary metal-oxide semiconductor or CMOS circuitry, such as one or more logic circuits. The formation of CMOS logic circuitry such as n-type and p-type transistors is known to those skilled in the art and thus is not described further herein.

An insulator 104 is then deposited onto the substrate 102. According to an exemplary embodiment, the insulator 104 is an oxide material. By way of example only, the oxide material can be a thermally grown silicon oxide if substrate 102 is silicon, or a deposited oxide or nitride by physical vapor deposition (PVD) or chemical vapor deposition (CVD).

Next, in step 130 gate trenches 106 are formed in the insulator 104. Standard lithography and etching techniques may be used to pattern the gate trenches 106. A suitable etching technique includes, but is not limited to, reactive ion etching or RIE. As shown in FIG. 1, the gate trenches 106 are formed extending partway through the insulator 104. Namely, a portion of the insulator 104 will remain at the bottom of the gate trenches 106, separating the gate trenches 106 from the substrate 102. This remaining material at the bottom of the gate trenches 106 will likewise separate the local gates (formed below) from the substrate. As a result, the local gates will be fully embedded in the insulator 104.

As shown in step 140, a gate conductor is next deposited into and filling the gate trenches 106. Suitable gate conductors include, but are not limited to, doped poly-silicon and/or a metal or combination of metals. Suitable gate metals include, but are not limited to, titanium nitride (TiN), tantalum nitride (TaN), tungsten (W), and Copper (Cu). Excess gate conductor overfilling the gate trenches 106 can be removed using a process such as chemical mechanical polishing or CMP. With this process, the insulator 104 acts as an etch stop. The result is the formation of local embedded gates 108.

As shown in FIG. 1, the CMP provides a flat surface on which the remaining layers of the sensor (e.g., the gate dielectric, semiconductor layer, etc.) can be built. Namely, post-CMP, the top surfaces of the local embedded gates 108 are coplanar with the top surface of the insulator 104. Having a flat, coplanar surface is important since it avoids introducing any physical distortions to the overlying materials which can negatively affect carrier transport. See, for example, U.S. Pat. No. 8,124,463 issued to Chen et al., entitled "Local Bottom Gates for graphene and Carbon Nanotube Devices," the contents of which are incorporated by reference as if fully set forth herein.

As shown in step 150, a gate dielectric 110 is then deposited onto the insulator 104/gates 108. Suitable gate dielectrics include, but are not limited to, silicon dioxide ($SiO_2$), and high-κ dielectrics such as hafnium oxide ($HfO_2$) and/or aluminum oxide ($AlO_2$). The term "high-κ," as used herein and as known in the art, refers to a material having a relative dielectric constant κ which is higher than that of $SiO_2$. For instance, $HfO_2$ has a dielectric constant κ=25 as compared to κ=4 for $SiO_2$. A process such as atomic layer deposition (ALD) or CVD may be used to deposit the dielectric material.

As shown in step 160, a channel material is next deposited onto the gate dielectric 110 over the local embedded gates 108. According to an exemplary embodiment, the channel material is selected from the group including carbon nanotubes, graphene, nanowires, nanosheets, and combinations thereof.

Deposition of the channel material onto a gate dielectric 110 can be accomplished in a variety of different ways, varying for instance based on the particular material being used. For instance, a casting process (e.g., spin-coating, spray-coating, etc.) can be used to deposit carbon nanotubes from a solution. See, for example, U.S. Patent Application Publication Number 2011/0048508 by Afzali-Ardakani et al., entitled "Doping of Carbon Nanotube Films for the Fabrication of Transparent Electrodes," the contents of which are incorporated by reference as if fully set forth herein. Functionalization of the carbon nanotubes may also be employed for their selective placement on the substrate via directed self-assembly. See, for example, U.S. Patent Application Publication Number 2014/0363643 by Afzali-Ardakani et al., entitled "Surface-Selective Carbon Nanotube Deposition Via Polymer-Mediated Assembly," the contents of which are incorporated by reference as if fully set forth herein. Selective placement may also be achieved by depositing the carbon nanotubes through a mask.

Graphene produced on another substrate can be transferred to the sensor using a lift-off technique. See, for example, U.S. Pat. No. 8,293,607 issued to Afzali-Ardakani et al., entitled "Doped Graphene Films with Reduced Sheet Resistance," the contents of which are incorporated by reference as if fully set forth herein.

Nanowires or nanosheets can be formed from a variety of different semiconductor materials, such as silicon, silicon germanium, etc. Nanowires or nanosheets fabricated on a donor substrate can be transferred to the present sensor structure using techniques such as transfer printing. See, for example, U.S. Patent Application Publication Number 2012/0031551 by Hsu, entitled "Method for Transfer Printing Nanowires," the contents of which are incorporated by reference as if fully set forth herein. The difference between nanowires and nanosheets is primarily based on their dimensions. For instance, when the structures have a smaller width (e.g., of from about 2 nanometers (nm) to about 10 nm, and ranges therebetween) then they are referred to as nanowires, whereas those having a larger width (e.g., of greater than 10 nm) are referred to as nanosheets. The distinction between nanowires and sheets is however somewhat arbitrary since they are processed herein in the same manner regardless.

The present field effect transistor (FET)-based sensors can be configured as chemical and/or biosensors to detect a variety of different molecules from gasses and chemical compounds to biological samples. In general, each FET-based sensor includes a channel material interconnecting source and drain electrodes (see below). The channel material is functionalized to react with certain target molecules. By way of example only, the surface of the channel material can be chemically functionalized with different chemical groups, enzymes, nucleic acids, antibodies, etc. When the target molecules are absorbed onto the surface, the resistance of the channel changes which shifts the threshold voltage Vt of the FET, thus changing the output current. This change in resistance can be correlated with the presence and/or amount of the target molecules present in a sample. See, for example, U.S. Pat. No. 9,091,648 issued to Afzali-Ardakani et al., entitled "Carbon Based Biosensors and Processes of Manufacturing the Same," the contents of which are incorporated by reference as if fully set forth herein. It is this resistance change that makes up the signals obtained from the sensors (see below).

The ability to create specific chemical and biosensors is known generally in the art. See, for example, Kichambare et al., "Biosensing using Carbon Nanotube Field-effect Transistors," Nanotechnologies for the Life Sciences, Vol. 8, pgs. 1-26 (September 2007), the contents of which are incorporated by reference as if fully set forth herein. The present techniques address that technology, and focus primarily on effective and efficient techniques for operating and retrieving data from arrays of these sensors.

Further, arrays are anticipated herein where the sensors are configured to detect different target molecules. For instance, in the example provided below, sensors are included in the array that are sensitive to a variety of different target molecules, e.g., a combination of multiple chemical and/or biological sensing capabilities. Similarly, each sensor itself can be sensitive to different target molecules. Namely, as would be apparent to one skilled in the art, the particular surface functionalization employed can be used to impart sensitivity to multiple target molecules.

Once deposited, the channel material can be patterned into individual channels 112 over each of the local embedded gates 108. See FIG. 1. Standard lithography and etching techniques can be employed. This patterning may be optional in some cases, for instance, where directed self-assembly is employed, the material is deposited through a mask, etc.

In step 170, source and drain electrodes 114 are formed in contact with opposite ends of the channels 112. Suitable source and drain electrode metals include, but are not limited to, nickel (Ni) and platinum (Pt). Standard metallization processes may be used to form the source and drain electrodes 114. The source and drain electrodes 114 complete the sensor fabrication process. As provided above, the substrate 102 may include pre-fabricated CMOS circuitry. In that case, interconnects (not shown) may be formed connecting the sensors to the CMOS circuitry.

Figure 2:
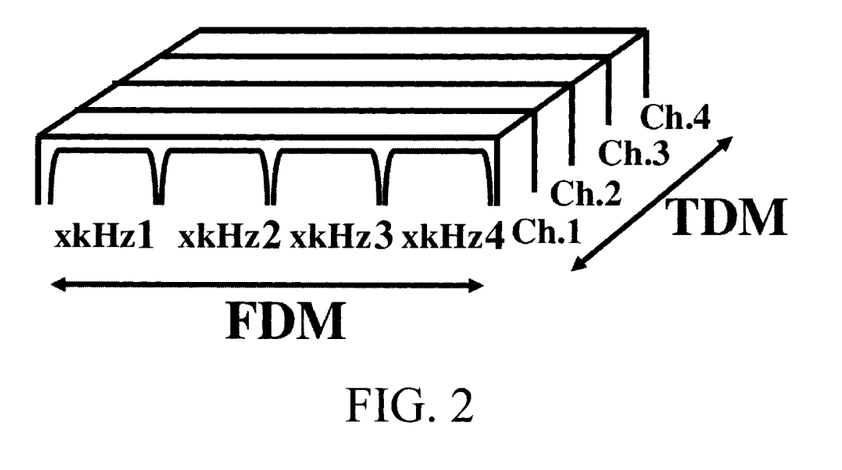
FIG. 2 is a schematic diagram illustrating multiplexing techniques like frequency division multiplexing (FDM) and time division multiplexing (TDM) being implemented to achieve a high data throughput from the sensor array according to an embodiment of the present invention.

As provided above, the present techniques address how to effectively and efficiently read out data from arrays of the above-described chemical/biosensors. Because of the large number of sensors in the array, the required time to read out data from the whole array becomes very long. For example, an array which has 5,000 sensors and 1 second sampling time (1 Hz band width) for each sensor will need 1.4 hours to scan through individual sensors. Thus, high throughput of data output is highly desired for a high density sensor array. For arrays of the present sensors, multiplexing techniques like frequency division multiplexing (FDM) and time division multiplexing (TDM) are implemented to achieve a high data throughput. See, for example, FIG. 2. As shown schematically in FIG. 2 and as will be described in detail below, the present sensor arrays are divided into multiple readout channels (e.g., Ch.1, Ch.2, . . . , Ch.4). Each channel represents one channel in TDM. Further, as shown in FIG. 2, for each channel there are multiple sensors where each sensor in the channel has its embedded gate voltage running at different frequencies (e.g., xkHz1, xkHz2, . . . , xkHz4).

In addition, 1/f noise is the dominate noise source in FET based sensors since the conventional FET based sensors forego a top gate electrode so as to expose the gate dielectric or channel material directly to the solution. Thus, conventional FET based sensors need to run at direct current (DC) and suffer from the highest 1/f noise and low signal-to-noise ratio.

Advantageously, the present unique embedded gate structure for FET-based sensors provides solutions to both noise and data throughput issues. Namely, the present sensors have an embedded gate to modulate the sensor to a higher frequency. And, as shown in FIG. 2, each sensor in one TDM channel can be modulated at different frequencies.

Figure 3:
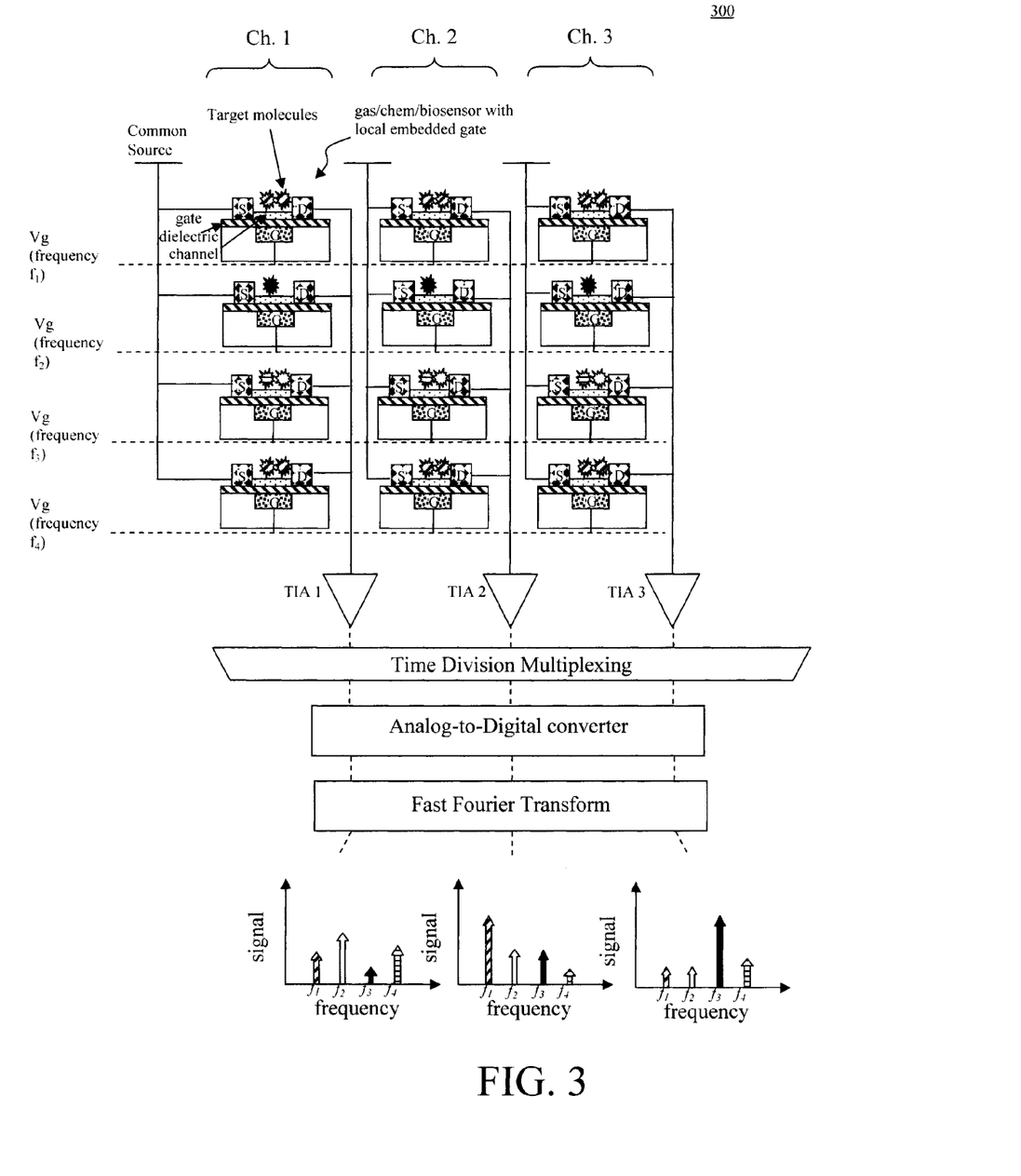
FIG. 3 is a diagram illustrating an exemplary sensor device array according to an embodiment of the present invention.
Figure 4:
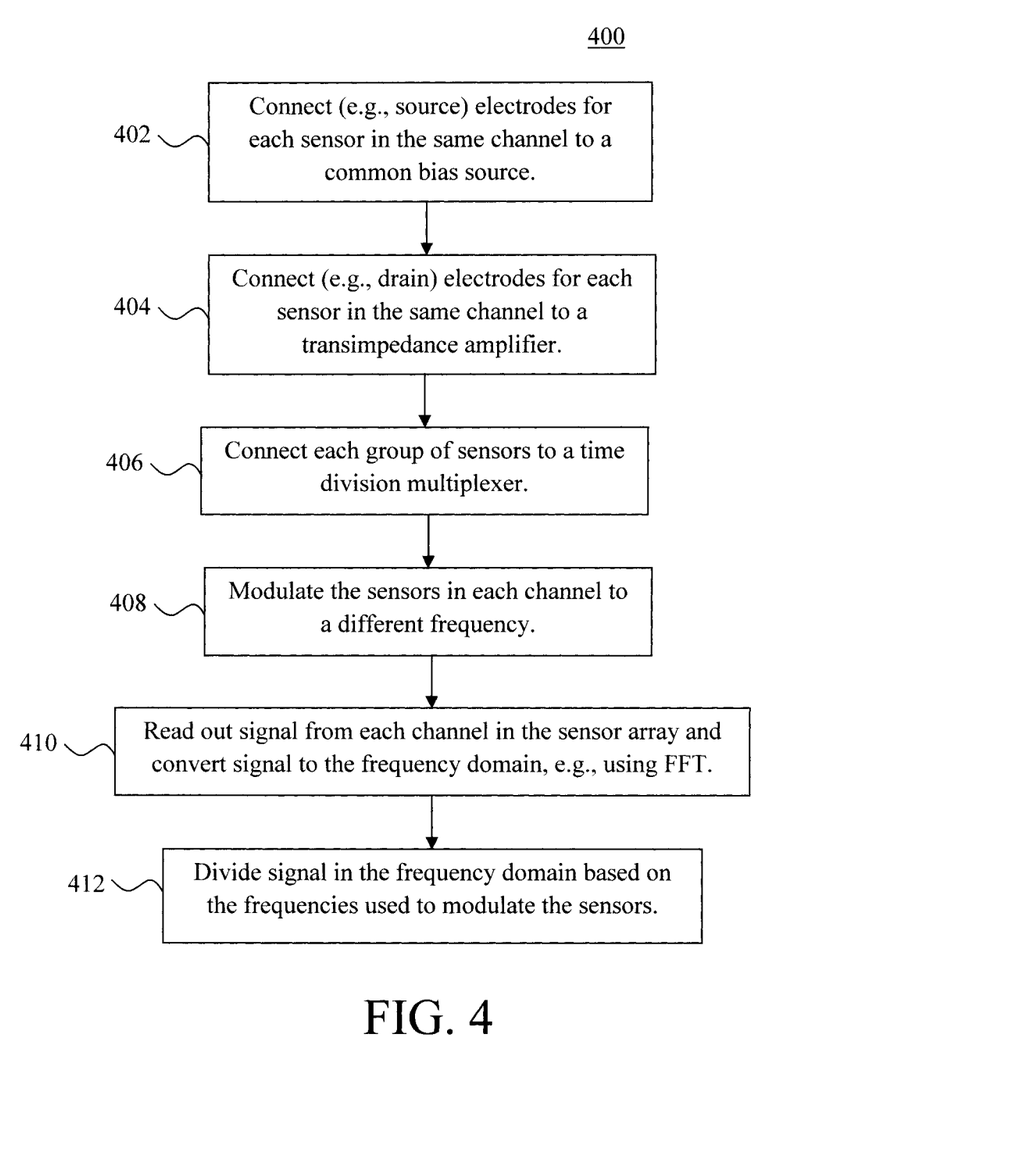
FIG. 4 is a diagram illustrating an exemplary sensing method according to an embodiment of the present invention.

Techniques for operating an array of the above-described sensors are now described by way of reference to FIG. 3 and FIG. 4. Referring to FIG. 3, an array 300 of sensors is shown. Each of the sensors in the array is fabricated according to methodology 100 of FIG. 1—see above. Based on the above-described process, each of the sensors in the array will have a local embedded gate (G) separated from a channel material by a gate dielectric, and source (S) and drain (D) electrodes contacting opposite sides of the channel material. For consistency, the same patterns are used to denote like structures in the figures.

FIG. 3 further illustrates how, as highlighted above, the sensors in the array are grouped into multiple channels. For ease and clarity of description, reference will be made herein to columns and rows of the sensor array, wherein each column represents a different channel. For instance, the array depicted in the present example includes three columns of sensors, each column containing four rows of sensors. As will be described in detail below, this grouping of sensors enables the present FDM techniques to be employed wherein each of the sensors in a given group/channel (e.g., each row of sensors within a given column) is modulated to a different frequency (e.g., f1, f2, etc.). Being able to independently modulate the frequency of individual sensors in the array is achieved using the local embedded gates.

FIG. 4 depicts an exemplary methodology 400 for operating sensor array 300. In step 402 of methodology 400 one electrode (e.g., the source electrode) from each sensor in a same given channel are tied together and connected to a single bias source. For instance, in the example depicted in FIG. 3, the source electrodes (S) of each sensor in the same channel (Ch. 1, Ch. 2, etc.) are tied together and connected to a common bias source. Specifically, referring to the leftmost column (Ch. 1) of sensors, the source electrodes (S) of the sensors in that column (via the source contacts) are interconnected. The same is true for the sensors in the next column over, and so on.

In step 404, another electrode (e.g., the drain electrode) from each sensor in a same given channel are tied together and connected to the input of a transimpedance amplifier. For instance, in the example depicted in FIG. 3, the drain electrodes (D) of each sensor in the same channel (Ch. 1, Ch. 2, etc.) are tied together and connected to an input of a transimpedance amplifier or TIA (TIA 1, TIA 2, etc.). Specifically, referring to the leftmost column (Ch. 1) of sensors, the drain electrodes (D) from the sensors in that column (via the drain contacts) are tied together and connected to a transimpedance amplifier TIA 1. The same is true for the sensors in the next column over, and so on. The transimpedance amplifiers TIA 1, TIA 2, etc. are preferably linear low noise amplifiers (LNAs).

In step 406, each group (e.g., column) of sensors is connected to a time division multiplexer. See also FIG. 3. Time division multiplexing generally involves receiving independent signals from different channels over a common path, and using synchronized switches to regulate the signals such that the signals appear in an alternating pattern in the path. A suitable time division multiplexing system for use in accordance with the present techniques is described, for example, in U.S. Pat. No. 3,575,557 issued to McCowen, entitled "Time Division Multiplex System," the contents of which are incorporated by reference as if fully set forth herein.

In step 408, the sensors in each channel (e.g., column of the array) are run at a different frequency. As described above, this is achieved using the embedded gates local to each of the sensors. Specifically, an alternating current (AC) gate voltage is applied at a different frequency to each of the sensors in a channel. See, for example, FIG. 3. For instance, as shown in FIG. 3, the gate voltage Vg is applied to each embedded local gate of the first row of sensors in each column at a first frequency f1, the gate voltage is applied to each embedded local gate of the second row of sensors in each column at a second frequency f2, and so on. This enables the signal output from the sensor array to be separated in the frequency domain via FDM. Standard circuitry can be used to provide the AC current at the desired frequency, e.g., via an external source or by the CMOS circuitry underneath the sensor array—see above. In the instant example, there are four different frequencies employed f1-f4. However, depending on the size of the array in practice there can be more frequency divisions, e.g., up to 64 divisions. According to an exemplary embodiment, the sensors are run at a range of frequencies right above the 1/f corner frequency (Fc) (the 1/f corner frequency is typically 0.1 kHz-100 kHz).

As provided above, the resistance changes (i.e., signals) that occur when the present FET-based sensors in the array come in contact with a particular target molecule are the signals processed via the present FDM and TDM-based techniques. While the signals from a given channel are connected to single output, since the sensors within each channel are modulated to a different frequency the signal read out from each channel can be separated in the frequency domain. Therefore, the signal from each sensor in the channel can be easily and rapidly discerned.

In the example depicted in the figures, the sensors in the array are configured to detect a variety of different molecules. For illustrative purposes only, four different target molecules are shown, each represented with a different pattern. Detection of the target molecules changes the output from the sensors.

Optionally, the outputs of the transimpedance amplifiers TIA 1, TIA 2, etc. can be connected to an additional signal conditioning channel, such as another amplifier and anti-aliasing filter. As is known in the art, an anti-aliasing filter can be used to restrict the bandwidth of a signal. This output is further connected to an analog-to-digital converter to digitize the signal. See FIG. 3.

In step 410, TDM (e.g., via the time-division multiplexer) is used to read out the signals from each channel in the sensor array. Algorithms such as fast Fourier Transform (FFT) can be used to convert the original time domain signal to the frequency domain. In step 410 the signals from all of the sensors within each TDM channel are read out all together. In step 412, however, the signals (from each channel) are divided in the frequency domain by reading signal tones at each frequency (e.g., f1-f4 see step 408) used to modulate the embedded gates. As a result, the resistance change signals resulting from the absorption of the target molecules onto individual sensors within each of the channels can be easily discerned. See FIG. 3.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A sensor device comprising:
  an array of field-effect transistor (FET)-based sensors, wherein the sensors are grouped into multiple channels, and wherein each of the sensors includes an insulator on a substrate, a local gate embedded in the insulator, a channel material over the local embedded gate, and source and drain electrodes in contact with opposite ends of the channel material, and wherein a surface of the channel material is functionalized to react with at least one target molecule;
  transimpedance amplifiers connected to outputs of the channels; and
  a time division multiplexer connected to outputs of the transimpedance amplifiers,
  wherein the source electrodes of the sensors in a given one of the channels are interconnected, and wherein the drain electrodes of sensors in the given channel are interconnected to a given one of the transimpedance amplifiers,
  wherein the sensors in a given channel are connected to a voltage source configured to provide a gate voltage of a different frequency to each of the sensors in the given channel such that each sensor in the given channel is run at the different frequency for frequency division multiplexing, and wherein the voltage source is configured to provide a gate voltage of a same frequency to the sensors in different channels.

2. The sensor device of claim 1, wherein each of the sensors further comprises:
  a gate dielectric between the local gate and the channel material.

3. The sensor device of claim 1, wherein the channel material is selected from the group consisting of: carbon nanotubes, graphene, nanowires, nanosheets, and combinations thereof.

4. The sensor device of claim 1, wherein at least one of the sensors is a biosensor.

5. The sensor device of claim 1, wherein at least one of the sensors is a chemical sensor.

6. The sensor device of claim 1, wherein the local gate is a metal gate.

7. The sensor device of claim 1, wherein a top surface of the local gate is coplanar with a top surface of the insulator.

8. The sensor device of claim 1, wherein the transimpedance amplifiers are linear low noise amplifiers.

9. A sensing method, comprising the steps of:
  forming a sensor device comprising: i) an array of FET-based sensors, wherein the sensors are grouped into multiple channels, and wherein each of the sensors includes an insulator on a substrate, a local gate embedded in the insulator, a channel material over the local embedded gate, and source and drain electrodes in contact with opposite ends of the channel material, and wherein a surface of the channel material is functionalized to react with at least one target molecule, ii) transimpedance amplifiers connected to outputs of the channels, and iii) a time division multiplexer connected to outputs of the transimpedance amplifiers;
  interconnecting the source electrodes of the sensors in a given one of the channels;
  interconnecting the drain electrodes of sensors in the given channel to a given one of the transimpedance amplifiers;
  providing a gate voltage of a different frequency to each of the sensors in the given channel such that each sensor in the given channel is run at the different frequency for frequency division multiplexing;
  providing a gate voltage of a same frequency to the sensors in different channels;
  reading a signal from the given channel; and
  dividing the signal in the frequency domain based on the different frequency used to modulate the sensors.

10. The method of claim 9, wherein the signal is read from the given channel using time-division multiplexing performed using the time division multiplexer.

11. The method of claim 9, further comprising the step of:
  converting the signal to the frequency domain.

12. The method of claim 11, wherein the signal is converted to the frequency domain using a fast Fourier transform.

13. The method of claim 9, further comprising the step of:
reading the signal at each of the different frequencies used to modulate the sensors.

14. The method of claim 9, wherein the channel material is selected from the group consisting of: carbon nanotubes, graphene, nanowires, nanosheets, and combinations thereof.

15. The method of claim 9, wherein at least one of the sensors is a biosensor.

16. The method of claim 9, wherein at least one of the sensors is a chemical sensor.

17. The method of claim 9, wherein the local gate is a metal gate.

18. The method of claim 9, wherein a top surface of the local gate is coplanar with a top surface of the insulator.

19. The method of claim 9, wherein the transimpedance amplifiers are linear low noise amplifiers.

* * * * *